United States Patent
Greiner-Perth et al.

(10) Patent No.: US 9,204,994 B2
(45) Date of Patent: Dec. 8, 2015

(54) DISCHARGE DEVICE

(75) Inventors: Juergen Greiner-Perth, Gottmadigen (DE); Matthias Wochele, Rielasingen-Worblingen (DE)

(73) Assignee: APTAR RADOLFZELL GMBH, Radolfzell (DE)

(*) Notice: Subject to any disclaimer, the term of this patent is extended or adjusted under 35 U.S.C. 154(b) by 154 days.

(21) Appl. No.: 13/877,483

(22) PCT Filed: Sep. 27, 2011

(86) PCT No.: PCT/EP2011/066778
§ 371 (c)(1),
(2), (4) Date: Apr. 3, 2013

(87) PCT Pub. No.: WO2012/045614
PCT Pub. Date: Apr. 12, 2012

(65) Prior Publication Data
US 2013/0190703 A1 Jul. 25, 2013

(30) Foreign Application Priority Data
Oct. 4, 2010 (DE) .......... 10 2010 048 085

(51) Int. Cl.
*A61F 9/00* (2006.01)
*B05B 11/00* (2006.01)
(Continued)

(52) U.S. Cl.
CPC ............. *A61F 9/0008* (2013.01); *A61F 9/0017* (2013.01); *A61M 5/2033* (2013.01);
(Continued)

(58) Field of Classification Search
CPC .. A61F 9/0008; A61F 9/0017; A61M 5/2033; B05B 11/0067; B05B 11/02; B05B 11/307; B05B 11/309; B05B 11/3091; B05B 11/3073; B05B 11/3074; B05B 11/3076; B05B 11/3004; B05B 11/3001; B05B 11/0072; B05B 11/3002; B05B 11/3009; B05B 11/3011; B05B 11/3012; B05B 11/3014; B05B 11/3015; B05B 11/3016; B05B 11/3018; B05B 11/3019; B05B 11/304; B05B 11/306; B05B 11/0048; B05B 11/0005; B05B 11/3038; B05B 11/3039; B05B 11/3059; B65D 81/20; B65D 81/2046; B65D 81/2053; B65D 83/14; B65D 83/16; B65D 83/20; B65D 83/42; B65D 83/46; B65D 83/48; B65D 83/0044; B65D 2255/00; B65D 2255/20; B65D 83/22; B65D 83/226; B65D 2519/00611; B65D 2519/00661; B65D 23/0857; A45D 34/00; A45D 40/00
See application file for complete search history.

(56) References Cited

U.S. PATENT DOCUMENTS 3,292,827 A * 12/1966 Frangos .................. 222/402.24
4,260,082 A * 4/1981 Rooney et al. ................ 222/340
(Continued)

FOREIGN PATENT DOCUMENTS

| CN | 101721306 A | 6/2010 |
|---|---|---|
| CN | 103328111 A | 9/2013 |

(Continued)

OTHER PUBLICATIONS

English translation of the first Office Action issued in Application No. 201180048414.6 dated Sep. 2, 2014 (2 pages).
(Continued)

*Primary Examiner* — Adam Marcetich
(74) *Attorney, Agent, or Firm* — Flynn, Thiel, Boutell & Tanis, P.C.

(57) ABSTRACT

A discharge device for discharging pharmaceutical liquids, with a housing, a liquid reservoir with a receiving space for storing the pharmaceutical liquid, and a discharge opening which is provided on the housing and which connects the receiving space to an environment and serves to dispense the pharmaceutical liquid. A pretensioned spring mechanism is provided, by means of which liquid in the receiving space of the liquid reservoir is subjected to pressure and which, in the assembled state of the discharge device, is not accessible for input of energy.

11 Claims, 3 Drawing Sheets

(51) Int. Cl.
*B65D 83/00* (2006.01)
*A61M 5/20* (2006.01)
*B05B 11/02* (2006.01)
*B65D 83/46* (2006.01)
*B65D 83/48* (2006.01)

(52) U.S. Cl.
CPC ......... *B05B11/0048* (2013.01); *B05B 11/0067* (2013.01); *B05B 11/02* (2013.01); *B05B 11/3001* (2013.01); *B05B 11/304* (2013.01); *B05B 11/306* (2013.01); *B05B 11/307* (2013.01); *B05B 11/309* (2013.01); *B05B 11/3015* (2013.01); *B05B 11/3038* (2013.01); *B05B 11/3059* (2013.01); *B05B 11/3074* (2013.01); *B05B 11/3091* (2013.01); *B65D 83/0044* (2013.01); *B65D 83/46* (2013.01); *B65D 83/48* (2013.01); *B65D 2255/00* (2013.01)

(56) References Cited

U.S. PATENT DOCUMENTS

| | | | |
|---|---|---|---|
| 4,750,532 A * | 6/1988 | Grothoff | 141/27 |
| 4,762,475 A | 8/1988 | Fuchs | |
| 5,024,355 A | 6/1991 | Jouillat et al. | |
| 5,044,525 A | 9/1991 | McKinney | |
| 5,085,642 A | 2/1992 | Sarnoff et al. | |
| 5,769,283 A * | 6/1998 | Owada et al. | 222/402.2 |
| 5,842,605 A * | 12/1998 | Lehmkuhl | 222/95 |
| 6,010,036 A * | 1/2000 | Bougamont et al. | 222/183 |
| 6,250,509 B1 * | 6/2001 | Fuchs | 222/321.6 |
| 6,453,795 B1 * | 9/2002 | Eicher et al. | 92/23 |
| 7,226,435 B2 | 6/2007 | Darnell | |
| 8,616,418 B2 | 12/2013 | Painchaud et al. | |
| 2004/0015126 A1 | 1/2004 | Zierenberg et al. | |
| 2004/0129733 A1 * | 7/2004 | Schultz | 222/321.7 |
| 2004/0164186 A1 * | 8/2004 | Kladders et al. | 239/543 |
| 2005/0023300 A1 * | 2/2005 | Schultz | 222/383.1 |
| 2006/0011663 A1 * | 1/2006 | Greiner-Perth | 222/383.1 |
| 2006/0084921 A1 | 4/2006 | Darnell | |
| 2006/0285987 A1 | 12/2006 | Jaeger et al. | 417/572 |
| 2007/0145077 A1 * | 6/2007 | Harrold | 222/256 |
| 2007/0194050 A1 * | 8/2007 | Krampen et al. | 222/153.13 |
| 2008/0251542 A1 * | 10/2008 | Rossignol | 222/380 |
| 2009/0001102 A1 * | 1/2009 | Fang | 222/260 |
| 2010/0038385 A1 * | 2/2010 | Jasper | 222/402.1 |
| 2010/0116852 A1 | 5/2010 | Painchaud et al. | |
| 2010/0206908 A1 * | 8/2010 | Pruvot | 222/153.13 |
| 2012/0197219 A1 | 8/2012 | Scanlon et al. | |

FOREIGN PATENT DOCUMENTS

| | | |
|---|---|---|
| DE | 10 2005 049 531 A1 | 10/2006 |
| EP | 0 199 143 A1 | 10/1986 |
| EP | 0 378 935 A1 | 7/1990 |
| JP | 2-6870 A | 1/1990 |
| JP | 4-16190 U | 2/1992 |
| JP | 2008-516666 A | 5/2008 |
| WO | WO 97/42992 | 11/1997 |

OTHER PUBLICATIONS

English translation of a Search Report issued by the State Intellectual Property Office of People's Republic of China in Application No. 201180048414.6 dated Sep. 2, 2014 (2 pages).
Form PCT/ISA/210 International Search Report dated Dec. 13, 2011 (4 pages).
Office Action of German Patent Office issued in German Application No. 10 2010 048 085.1 dated Jun. 7, 2011 (8 pages).
English translation of Notice of Reason for Rejection of Japanese Patent Office issued in Application No. 2013-532121 dated May 15, 2015 (4 pages).

* cited by examiner

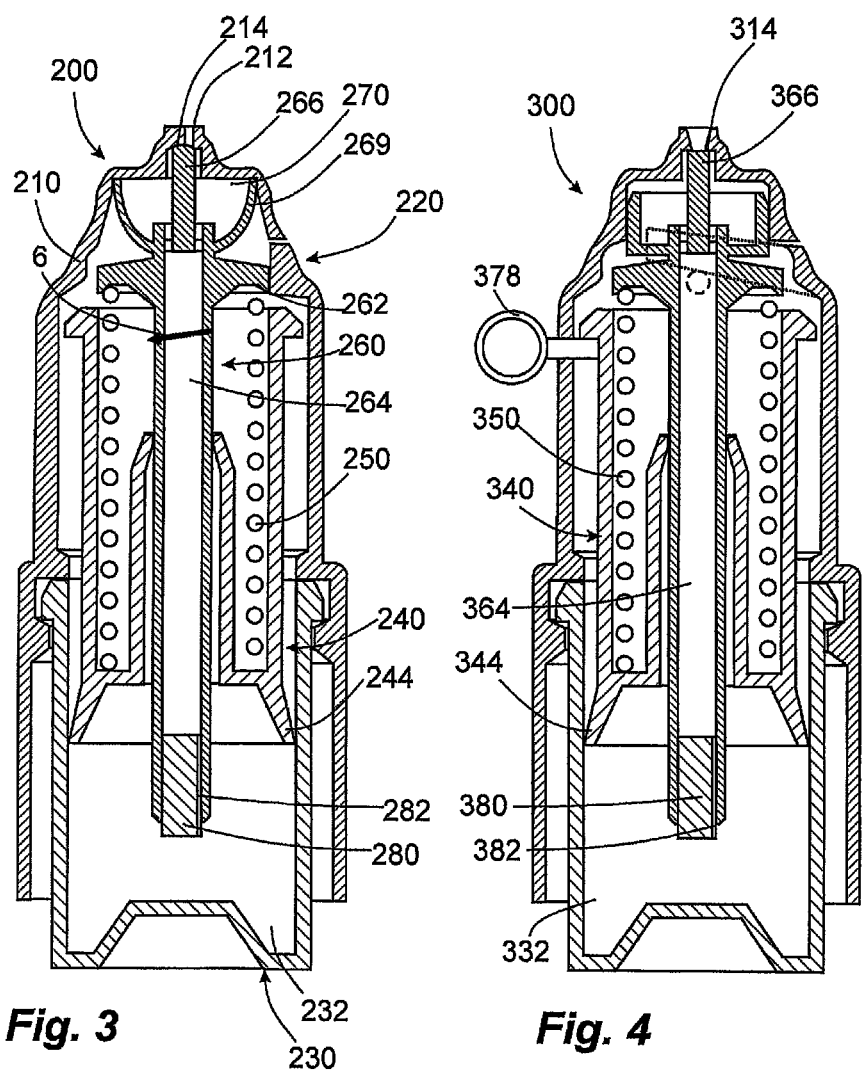

DISCHARGE DEVICE

FIELD OF APPLICATION AND PRIOR ART

The invention relates to a discharge device for discharging pharmaceutical liquids, in particular for ophthalmic use, having a housing, a liquid reservoir with a receiving space for storing the pharmaceutical liquid prior to discharge and a discharge opening provided on the housing which connects the receiving space to the environment and which serves to dispense the pharmaceutical liquid.

Generic discharge devices are well-known from the prior art. Such generic discharge devices require an overpressure in order to supply the pharmaceutical liquid from the receiving space to the discharge device. With numerous of the well-known discharge devices, actuation is effected such that said pressure is invoked manually, for example by actuating a pump acting as supply device or by compressing the liquid reservoir per se and a thereby achieved pressure increase in the receiving space.

In the case of many known discharge devices this pressure generated for liquid discharge is also used to thereby open a pressure-controlled outlet valve which seals the discharge opening of the discharge device in the idle state.

However, in particular in the case of discharge devices for ophthalmic use, a low liquid pressure at the discharge opening is desired, so that a pressure-controlled outlet valve provided there is hard to realize since it needs to be capable of switching between a reliably closing state and a reliably opening state by means of only a small difference between two pressures.

OBJECT AND SOLUTION

Therefore, it is primarily the object of the present invention to further develop a generic discharge device such that it provides improved discharge devices, in particular for discharging liquid in the form of drops.

According to the invention, this is achieved in that a pre-stressed spring device is provided on a discharge device according to the invention, by means of which liquid is pressurized in the receiving space of the liquid reservoir and which in the mounted state of the discharge device is not accessible for introduction of energy.

Thus, in the case of a discharge device according to the invention, pressure is applied to the liquid in the liquid reservoir by means of a spring device in which mechanical work is stored. Since the liquid is pressurized as from the moment of the initial operation, it is to be reliably ensured that said pressure application alone does not invoke liquid to leak from the discharge opening. Measures therefor will be explained in the following.

According to the invention, the spring device of a discharge device according to the invention is not accessible for the introduction of energy in the assembled state of the discharge device. Thus, in a condition of the discharge device as supplied to the customer in which the different component parts of the discharge device have already been assembled, a further tensioning of the spring device is not possible. Instead, the spring device is completely tensioned even prior to delivery and this energy stored in the spring is gradually utilized during the use for dispensing liquid.

The mechanical work which can be stored in a conventional spring in the field of discharge devices is not very high. However, this is of little importance in particular in view of the preferred purpose of application of the droplet dispenser since even very small energy amounts are sufficient for dispensing the liquid with an overpressure of between 100 and 300 mbar, as common with droppers.

It is particularly preferred when an outlet valve which can be actuated manually by means of an actuation handle is provided for a discharge device according to the invention, which valve is arranged between the receiving space and the discharge opening. Such a manually actuatable outlet valve can be kept closed by means of comparatively strong springs in the closed state since overcoming of a spring force of such a strong spring (for example between 3 and 10 Newton) is readily possible by a manual actuation. Liquid only slightly over-pressurized, however, may overcome such a spring force only in case of very large pressure application areas which can be integrated in handy and portable discharge devices only with difficulty.

Thus, in the case of a discharge device according to said embodiment, the medium is permanently and up to the outlet valve pressurized by means of the pressure generated by the spring device. Upon manual actuation of the outlet valve and opening of said valve, the liquid passes the discharge opening under the preferably slight overpressure and therein forms drops there for ophthalmic application.

In the case of a further embodiment of the invention, it is provided that the discharge device is configured for dispensing the liquid in the form of droplets. To that end, it is preferably in particular provided that with actuation for intended use, the liquid streams outside through the discharge opening only with a very low overpressure of preferably less than 500 mbar, in particular preferred with an overpressure between 100 mbar and 300 mbar. As mentioned above, such a low overpressure can be achieved directly by means of the spring device for pressure application to the liquid reservoir. However, it is also possible to configure a stronger spring device and thus a higher pressure developing in the receiving space, wherein in such a case preferably a throttle device is provided between the liquid reservoir and the outlet valve, which causes a pressure reduction in the aforementioned preferred pressure range.

Different types of springs can be considered as spring device for pressure application to the liquid reservoir, for example also gas pressure springs. Pressure application can be effected by compressing a liquid reservoir deformable per se, such as a bag or a bellows, for example.

However, it is preferred that the spring device is a liquid reservoir spring in the type of an elastically deformable spring, by means of which the liquid in the receiving space is pressurized, wherein the liquid reservoir spring in particular acts on a piston which limits the receiving space in one direction and is slidably movable in the liquid reservoir.

Such a liquid reservoir spring can, for example, be configured as a helical spring. A particularly obvious configuration involves the use of a metallic spring for that purpose. However, also other springs are suitable for said purpose, in particular for example plastic springs, wherein such a plastic spring can in particular be an integral part of the piston, and thus allows a very simple and cost-efficient construction.

It is of particular advantage if the piston limits the receiving space on the side facing the discharge opening and if the spring device is configured and/or arranged such that it applies force to the piston in a direction away from the discharge opening. Thus, in such a configuration, the force application to the liquid by the piston is effected in a direction opposed to the flow direction of the liquid from the receiving space of the liquid reservoir to the discharge opening. As a result, in particular a construction can be realized according to which the liquid reservoir is configured as a component separate from the housing and connectable thereto, wherein the piston is movably secured to the housing even prior to connecting the liquid reservoir to the housing. In such a configuration, the liquid reservoir can be configured in a very simple manner, in particular as an integral, bowl-type component which during attaching to the housing of the discharge device at the same time receives the piston provided on the assembly group of the housing. This is advantageous in particular in view of a method for introducing spring energy into the spring device that will be described in the following.

In the configuration in which the movement direction of the piston is opposed to the movement direction of the liquid from the receiving space to the discharge opening, it is considered to be particularly preferred if the piston is slidably movable guided on a hollow tube in a sliding manner, which tube interconnects the receiving space of the liquid reservoir and the discharge opening. Thus, said hollow tube assumes two functions therein. On the one hand, it leads the liquid past the piston in the direction of the discharge opening. On the other hand, it represents a guidance for the piston, in particular for a time period prior to the assembling of the discharge device when the piston is not yet guided inside the liquid reservoir.

It is particularly preferred if the hollow tube is configured integrally with a valve body of the outlet valve or if it is fixedly connected thereto. As a result of such a configuration, a design of the discharge device involving only a few components is possible, since there is no need to use two distinct parts for the valve body and the hollow tube.

In a particularly preferred configuration, in which the piston is retained on the housing in a movable manner, it is furthermore provided that the housing and the relative movability of the piston in relation to the housing are matched to one another such that the piston is not displaceable or is only slightly displaceable (less than 10 mm) beyond the end of the housing facing away from the discharge opening in relation to said housing. Preferably, this is achieved in that the housing comprises a circumferential skirt or other types of protective webs on the side facing away from the discharge opening, thus presenting a protection for the piston before the piston is inserted in the liquid reservoir during the assembling. Said protection, which is achieved by means of the housing and the limited relative movability of the piston, is in particular advantageous if the components of the discharge device are handled as bulk material prior to the assembling, so that without a protection for the piston, damage to the piston and thus later leakage could occur.

In a particularly preferred configuration, a valve body is provided at the outlet valve, wherein said valve body is applied with force in the direction of a closed state by means of a valve spring. In this case, the valve spring is preferably identical to the spring device for pressure application to the liquid, in particular to the aforementioned liquid storage spring. A valve spring for force application to the valve body in the direction of its closed state is also of advantage in the case of a configuration of the discharge device in which the opening of the outlet valve is directly achieved mechanically by means of a handle, since thereby the closed state is reliably reestablished after releasing the handle. As a result of the use of a common spring for pressure application to the liquid in the receiving space and for closing the outlet valve, a discharge device according to the invention can be configured with a very small number of parts.

However, since a spring for closing the outlet valve can be configured comparatively strong, in particular in case of an outlet valve which is opened manually by means of a handle, and therefore also the liquid pressure in the receiving space generated by said spring can be comparatively high, it can be advantageous to provide a throttle device, as described above, in particular in such a configuration including only one spring for the outlet valve and for pressure application to the liquid.

Generally it is possible in the case of a discharge device according to the invention to provide the pressure application to the liquid by means of the spring device tensioned in the course of assembling even as from the time of assembly. However, a higher degree of safety against undesired discharge of liquid even prior to the initial operation by the final customer can be achieved in that a safety means is provided which is accessible from the exterior and may be handled during the initial operation by means of which the spring device is kept in a pre-stressed state prior to the initial operation. Said safety means can be released by the final customer in the course of the initial operation so that not earlier than at that time the desired pressure application to the liquid in the receiving space is established.

Furthermore, the invention relates to an assembly method for a discharge device for pharmaceutical liquids, wherein the discharge devices comprises a first assembly group having a housing with an outlet opening and a manually actuatable outlet valve, a second assembly group having a liquid reservoir with a receiving space for receiving the liquid and a spring device pressurizing the liquid in the receiving space in the tensioned state after the assembling. In this case, according to the invention, starting from an initial state in which the housing and the liquid reservoir are present as separate assembly groups, the following sequence of steps is performed: At first, the receiving space of the liquid reservoir is filled with the pharmaceutical liquid. After that, the two assembly groups are interconnected, wherein by connecting the assembly groups, the spring device is stressed and thus the pressure for pressure application to the liquid in the receiving space is generated.

Thus, in the assembly method according to the invention, the energy which is subsequently stored in the spring device is introduced by joining the two assembly groups until said energy is used in the course of a discharge procedure or the course of filling of a pump chamber. In this manner, while joining the assembly groups, the spring device is tensioned at the same time. Subsequently, in order to reduce the pressure application to the liquid during the storage, a safety pin or the like can be used in order to keep the spring in the tensioned state. In this type of assembly, a separate step for tensioning the spring device is not required.

It is of particular advantage if the first assembly group comprises a piston and the aforementioned spring device, wherein after filling the receiving space in the first step the receiving space initially remains open on the end side and is closed to the environment not earlier than in the following step by inserting the piston into the liquid reservoir. A continued approaching movement of the assembly groups to connect the assembly groups then leads to a tensioning of the spring device after closing the receiving space by means of the piston.

BRIEF DESCRIPTION OF THE DRAWINGS

Further aspects and advantages of the present invention arise, besides from the claims, from the following description of preferred exemplary embodiments of the invention which are explained with reference to the drawings. In this case, the figures schematically show in:

DETAILED DESCRIPTION OF THE EXEMPLARY EMBODIMENTS

Figures 1A, 1B:
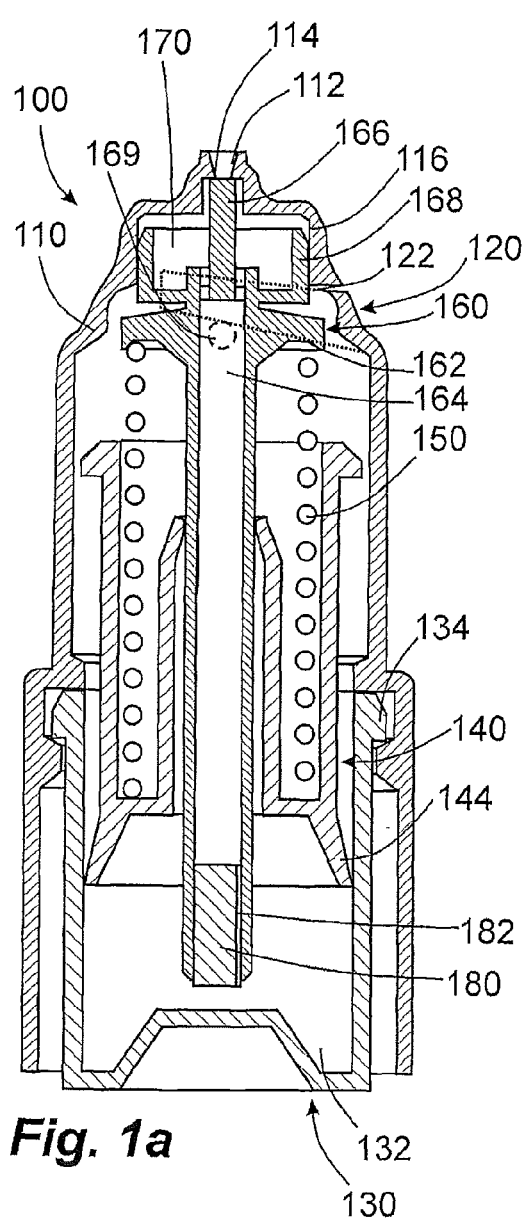
FIGS. 1a and 1b a first embodiment of a discharge device according to the invention prior to and during a discharge process, FIGS. 2a to 2c the discharge device of the FIGS. 1a and 1b in different states during the assembly, and FIGS. 3 and 4 variants with respect to the embodiment of FIGS. 1 and 2.

FIGS. 1a and 1b show a first embodiment of a discharge device 100 according to the invention.

With reference to the illustration of FIG. 1a, at first the individual components of the discharge device are explained. The discharge device 100 comprises a housing 110 which is essentially configured as a rotational body and which comprises a discharge opening 112 on an end face. On the opposite end, the housing 110 is configured to be open and limited by a liquid reservoir 130, which comprises a receiving space 132 for receiving a liquid to be discharged. The liquid reservoir 130 is engaged with the housing 110 by means of a snap-on connection 134 and is thus fixed in location to the housing during operation.

For volume reduction of the receiving space 132, the latter is limited upwards by means of a piston 140. Said piston 140, which limits the receiving space 132 by means of a piston lip 144, is permanently applied with a downward force by means of a spring 150 in order to exert a pressure on the liquid in the receiving space 132. The end of the spring 150, configured as helical spring, opposite to the piston 140 rests on an abutment face 162 which is part of a component 160 assuming multiple functions. Besides the provision of the support face 162 for the spring 150, the component 160 also forms a hollow channel 164 which extends from the receiving space 132 up to the region of the discharge opening 112. Above the support face 162, the component 160 comprises a valve body 166 which is pressed against a valve seat 114 on the inner face of the housing 110 by means of the spring 150. Liquid which during operation exits the hollow tube 164 on the upper end thereof enters the valve pre-chamber 170 which is limited by means of a slide collar 168 of the component 160 on the exterior, which collar per se is guided in a guidance section 116 on the inner face of the housing 110 in an essentially liquid-tight manner.

Thus, the spring 150 assumes a double function: It pressurizes the liquid in the receiving space 132 via the piston 140. Moreover, it keeps the outlet valve 114, 164 closed in an idle state of the discharge device 100.

For a better illustration, the liquid is not shown in the illustrations of FIGS. 1a and 1b. For the following explanation, it is understood that the receiving space 132, the hollow tube 164 and the valve pre-chamber 170 are already completely filled with liquid.

In the state of FIG. 1a, said liquid is under a homogenous pressure caused by the spring 150. Since the spring provides a comparatively high spring force of 8 Newton, the pressure of the liquid is approximately 1 bar prior to the beginning of the discharge process.

For discharging of liquid, an actuation handle 120, which is an integral part of the housing 110 and which can be pushed-in relative to the remaining housing 110 by means of free punches, is pushed-in in a manner shown by means of the arrow 2 in FIG. 1b, wherein by means of an actuation arm 122 indicated in a dotted contour and provided on the actuation handle 120, a bolt 169 provided on the constructional unit 160 is pushed downwards.

Together with the bolt 169, the entire constructional unit 160 is displaced in the direction of the arrow 4, wherein this results in an opening of the outlet valve 114, 164 against the force of the spring 150. By means of the opening of the outlet valve 114, 164 the pressure in the hollow tube 164 and the valve pre-chamber 170 breaks down immediately, since a further flowing of liquid from the receiving space 132 into the hollow tube 164 and the valve pre-chamber 170 is significantly limited, due to a throttle body 180 having a narrow throttle channel 182 with a free cross-section of less than 1 mm$^2$ which body is inserted in the hollow tube 164 on the lower end. The overpressure of 1 bar in the receiving space 132 is reduced to an overpressure of approximately 250 mbar in the hollow tube 164 and the valve pre-chamber 170 by means of the throttle channel 182 so that the liquid flows through the discharge opening 112 with a very low pressure and is thus suitable for forming drops at the discharge opening 112.

The shown and described discharge device 100 forms a discharge device formed by only a few components which can be produced by simple means which ensures safe handling and easily reproducible liquid discharge.

Furthermore, the described discharge device 100 is suitable for an advantageous assembly method, as explained in the following.

Figure 2A:
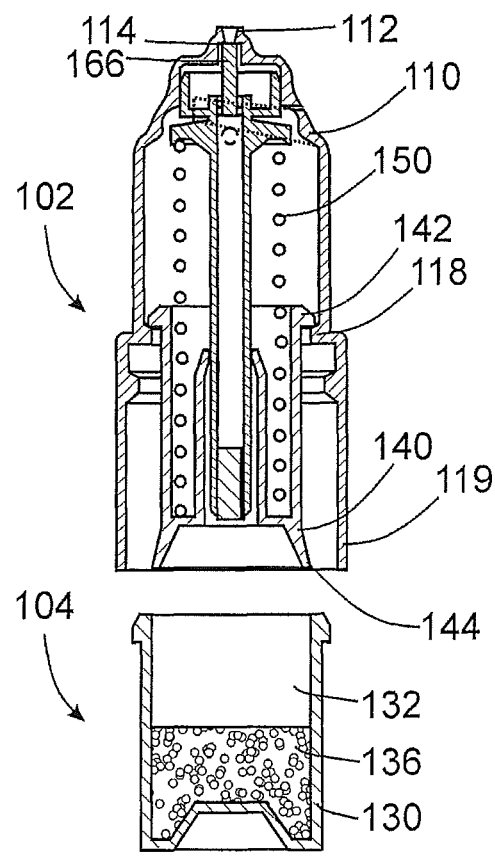
Figure 2B:
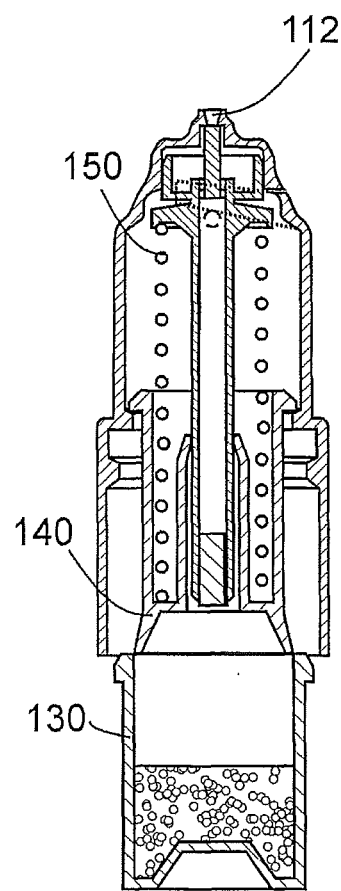

The assembly of the discharge device of the FIGS. 1a and 1b is explained with reference to the FIGS. 2a to 2c.

The starting point of the assembling are two separate assembly groups 102, 104, wherein the assembly group 102 comprises all components of the discharge device 100 except for the liquid reservoir 130. In particular the piston 140 is also part of the assembly group 102, wherein by means of an inward-projecting protrusion 118 on the housing 110 as well as an outward-projecting collar 142 on the piston 140 it is ensured that the piston 140 cannot be separated from the housing 110 despite the force of the spring 150. Instead, the piston is pressed in a lower end position by means of the spring 150 prior to joining the first assembly group 102 and the second assembly group 104, in which position it is protected by the configuration of the housing 110. This is achieved by a circumferential skirt 119 on the lower end of the housing 120 which projects downwards beyond the piston lip 144 of the piston 140. As a result, the piston 140 and in particular the piston lip 144 is protected also in case a multiplicity of assembly groups 102 is handled together as bulk material prior to the assembling.

For finishing the assembly device of FIG. 1a and FIG. 1b, at first the receiving space 132 of the liquid reservoir 130 is filled with a liquid 136. Subsequent thereto, the two assembly groups 102, 104 are approached until the piston 140 penetrates the liquid reservoir 130 by means of the piston lip 144, so that the piston lip 144 abuts circumferentially on the inner face of the liquid reservoir 130. This state is shown in FIG. 1b.

As from this time, liquid and air can escape only through the discharge opening 112, while the latter is kept closed during the assembly process by means of the spring 150. Along with the continued insertion of the assembly group 104 together with the liquid reservoir 130 in the assembly group 102, the piston 140 penetrates deeper into the liquid reservoir 130, whereby the spring 150 is tensioned and effects the pressure application to the liquid 136 already at this time.

Figure 2C:
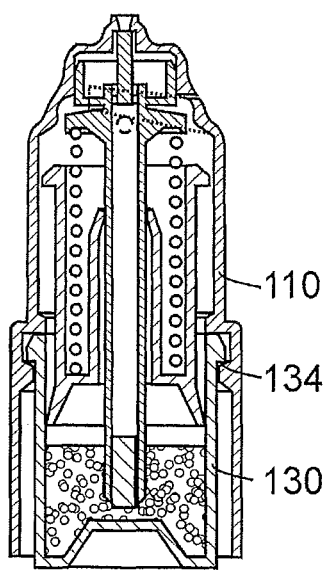

The assembling process is completed upon establishment of the snap connection 134 between the housing 110 and the liquid reservoir 130 in the manner shown in FIG. 2c. The discharge device is now in a delivery condition. By means of the comparatively strong spring 150 it is ensured that the outlet valve 114, 166 is kept closed until a discharge process is deliberately caused by a user by means of the handle 120.

Thus, the method described allows to insert the spring device 150, which later represents the energy source for discharging liquid from the discharge device 100, even during the assembling and without additionally-required steps.

FIGS. 3 and 4 show variations of the embodiments of FIGS. 1 and 2, wherein functionally similar or functionally identical components are concordant in terms of the last two digits of the reference numerals with the ones of the embodiment of FIGS. 1 and 2.

In the case of the embodiment of FIG. 3, the specific characteristic is in the type of actuation, Instead of displacing the constructional unit 260 according to the type of the embodiment of FIGS. 1 and 2 in the direction of the arrow 4 by means of the actuation handle 220, the constructional unit 260 is tilted in the direction of the arrow 6 by means of the actuation handle 220, whereby in response thereto the valve body 266 is slightly displaced in relation to the valve area 214 and thereby enables the discharge opening 212. Upon elimination of the actuation force to the actuation handle 222, the valve body 264 is moved back to the starting position shown in FIG. 3 in which it blocks the discharge opening 212, due to the shape design of the valve area 214 and under the effect of the spring 250 after omission of the actuation force. This manoeuvrability of the component 260 requires that, instead of the sliding collar 168 of the embodiment of FIGS. 1 and 2, a shape variable Icollar 269 be provided which keeps the valve pre-chamber 270 closed to the bottom even upon tilting of the component 260.

The discharge device 300 according to FIG. 4 is almost identical to the discharge device of FIGS. 1 and 2. The only difference is that a safety pin 378 is provided which in the inserted state of FIG. 4 prevents a displacement of the piston 340 under the effect of the spring force of the spring 350 in the direction of the receiving space 332 and thereby limits the pressure application to the liquid in the receiving space 332. The safety pin 378 is removed according to the intended use by the final user prior to an initial operation so that subsequently the same performance of the discharge device 300 as with the discharge device 100 of FIGS. 1 and 2 is obtained. However, up to this time, the liquid pressure is effectively limited by means of the safety pin so that the risk of an undesired leaking of liquid is further reduced.

The invention claimed is:

1. A discharge device for discharging a pharmaceutical liquid comprising:
a housing;
a liquid reservoir with a receiving space for storing the pharmaceutical liquid;
a discharge opening provided on the housing, the discharge opening connecting the receiving space to an environment and serving for dispensing the pharmaceutical liquid;
an outlet valve between the receiving space and the discharge opening;
a pre-tensioned spring device for pressurizing liquid in the receiving space of the liquid reservoir and up to the outlet valve, the pre-tensioned spring device being isolated from contact external of the discharge device for further pressurizing the liquid in the liquid reservoir in an assembled state of the discharge device; and
a safety member accessible from an exterior of the discharge device, the safety member holding the spring device in a pre-tensioned state prior to an initial operation;
the outlet valve being mechanically and directly openable by an actuation handle so that, upon manual opening of the outlet valve, the liquid pressurized by the spring device passes through the discharge opening, with pressure applied to the liquid by the spring device forcing the liquid through the discharge opening.

2. The discharge device according to claim 1, wherein the discharge device is configured for dispensing liquid in the form of drops.

3. The discharge device according to claim 1, wherein the spring device is an elastically deformable spring, and wherein the elastically deformable spring acts on a piston slidably moveable in the liquid reservoir and limiting the receiving space.

4. The discharge device according to claim 3, wherein the piston limits the receiving space on the side facing the discharge opening, and the spring device is configured and/or arranged such that the spring device 1 applies a force to the piston away from the discharge opening.

5. The discharge device according to claim 3, wherein the liquid reservoir is a component separate from the housing and connectable thereto, and the piston is movably secured on the housing.

6. The discharge device according to claim 3, wherein the piston is guided on a hollow tube in a slidable manner, the hollow tube connecting the receiving space of the liquid reservoir to the discharge opening.

7. The discharge device according to claim 3, wherein the housing and relative movability of the piston in relation to the housing are matched to one another such that the piston cannot be displaced beyond an end of the housing facing away from the discharge opening in relation to the housing.

8. The discharge device according to claim 1, wherein a valve spring applies a force against a valve body of the outlet valve in a direction of a closed state.

9. The discharge device according to claim 1, wherein movement of the actuation handle does not pressurize the liquid.

10. A method of assembling a discharge device for discharging pharmaceutical liquids, the discharge device comprising:
a housing;
a liquid reservoir with a receiving space for storing the pharmaceutical liquid;
a discharge opening provided on the housing, the discharge opening connecting the receiving space to an environment and serving for dispensing the pharmaceutical liquid;
an outlet valve between the receiving space and the discharge opening; and
a pre-tensioned spring device for pressurizing liquid in the receiving space of the liquid reservoir and up to the outlet valve, the pre-tensioned spring device being isolated from contact external of the discharge device for further pressurizing the liquid in the liquid reservoir in an assembled state of the discharge device;
the outlet valve being mechanically and directly openable by an actuation handle so that, upon manual opening of the outlet valve, the liquid pressurized by the spring device passes through the discharge opening, with pressure applied to the liquid by the spring device forcing the liquid through the discharge opening;
wherein the discharge device further comprises:
a first assembly group including the housing with the discharge opening and the outlet valve, and
a second assembly group with the liquid reservoir having the receiving space for receiving the liquid;
and wherein starting from an initial state, where the first assembly group and the second assembly group are present separately, the method comprises:

a. filling of the receiving space of the liquid reservoir with the pharmaceutical liquid; and
  b. connecting the first assembly group and the second assembly group such that the spring device is tensioned and thus pressure for pressure application to the liquid in the receiving space is generated.

11. The assembly method according to claim 10, wherein the first assembly group comprises a piston, wherein after filling the receiving space in step a, the receiving space initially remains open on one side and not earlier than in step b the receiving space is closed in relation to an exterior of the discharge device by inserting the piston into the liquid reservoir.

* * * * *